United States Patent
Sudsina et al.

[11] Patent Number: 6,004,345
[45] Date of Patent: Dec. 21, 1999

[54] THERAPEUTIC WRAP FOR SORE THROATS

[76] Inventors: Loretta A. Sudsina, 3712 Bevan Rd., North Versailles, Pa. 15137-2310; Donald J. Sudsina, H.C. 1 Box 153, Marienville, Pa. 16239; Karen Davis, Rte. 3 Box 352, New Cumberland, W. Va. 26047; Daniel Sudsina, 180 Magnus La., N. Huntingdon, Pa. 15642; Diana Bruno, 110 Rose Ave., Harrison City, Pa. 15636-9451; Donald R. Sudsina, 3712 Bevan Rd., North Versailles, Pa. 15137

[21] Appl. No.: 09/094,106

[22] Filed: Jun. 10, 1998

[51] Int. Cl.⁶ ........................................... A61F 7/00
[52] U.S. Cl. ............................... 607/108; 607/109
[58] Field of Search ............................. 607/96, 108, 109, 607/112; 2/207; D2/600, 602

[56] References Cited

U.S. PATENT DOCUMENTS

| | | |
|---|---|---|
| D. 342,790 | 12/1993 | Zona . |
| 4,321,709 | 3/1982 | Steinberg ..................................... 2/207 |
| 4,805,619 | 2/1989 | Swearingen . |
| 5,005,374 | 4/1991 | Spitler . |
| 5,088,549 | 2/1992 | Schneider . |
| 5,211,623 | 5/1993 | Sarkozi . |
| 5,247,928 | 9/1993 | Stilts, Jr. . |
| 5,395,399 | 3/1995 | Rosenwald . |
| 5,400,617 | 3/1995 | Ragonesi et al. . |
| 5,507,793 | 4/1996 | Hodges . |

FOREIGN PATENT DOCUMENTS

| | | |
|---|---|---|
| 718686 | 9/1965 | Canada . |
| 1126120 | 6/1982 | Canada . |

*Primary Examiner*—Lee Cohen
*Assistant Examiner*—Rosiland Kearney
*Attorney, Agent, or Firm*—Richard C. Litman

[57] ABSTRACT

A therapeutic wrap adapted to use with a vaporizing ointment for relieving the discomfort of colds and sore throats. The invention includes a therapeutic kit having a vaporizing ointment and a wrap. The wrap is composed of an elongated piece of fabric, preferably flannel. The fabric has a throat end and a chest end. The throat end has a width approximately corresponding to the length of a human neck. The chest end has a width greater than the width of the throat end. At least two mating portions of hook and loop fastener are attached to opposite surfaces of the fabric. The hook and loop fastener secures the wrap around the neck so that the chest end drapes over the chest. The wrap helps to keep the patient's neck and chest warm and protected from drafts so that the vaporizing ointment can have its maximum effect. The wrap also protects the patient's clothing. The wrap is comfortable, looks neat, and holds securely, so that the patient's mobility is enhanced. The invention includes a method of treating colds and sore throats by applying the vaporizing ointment to the neck and chest, covering the neck and chest with a wrap, and securing the wrap with hook and loop fastener.

7 Claims, 3 Drawing Sheets

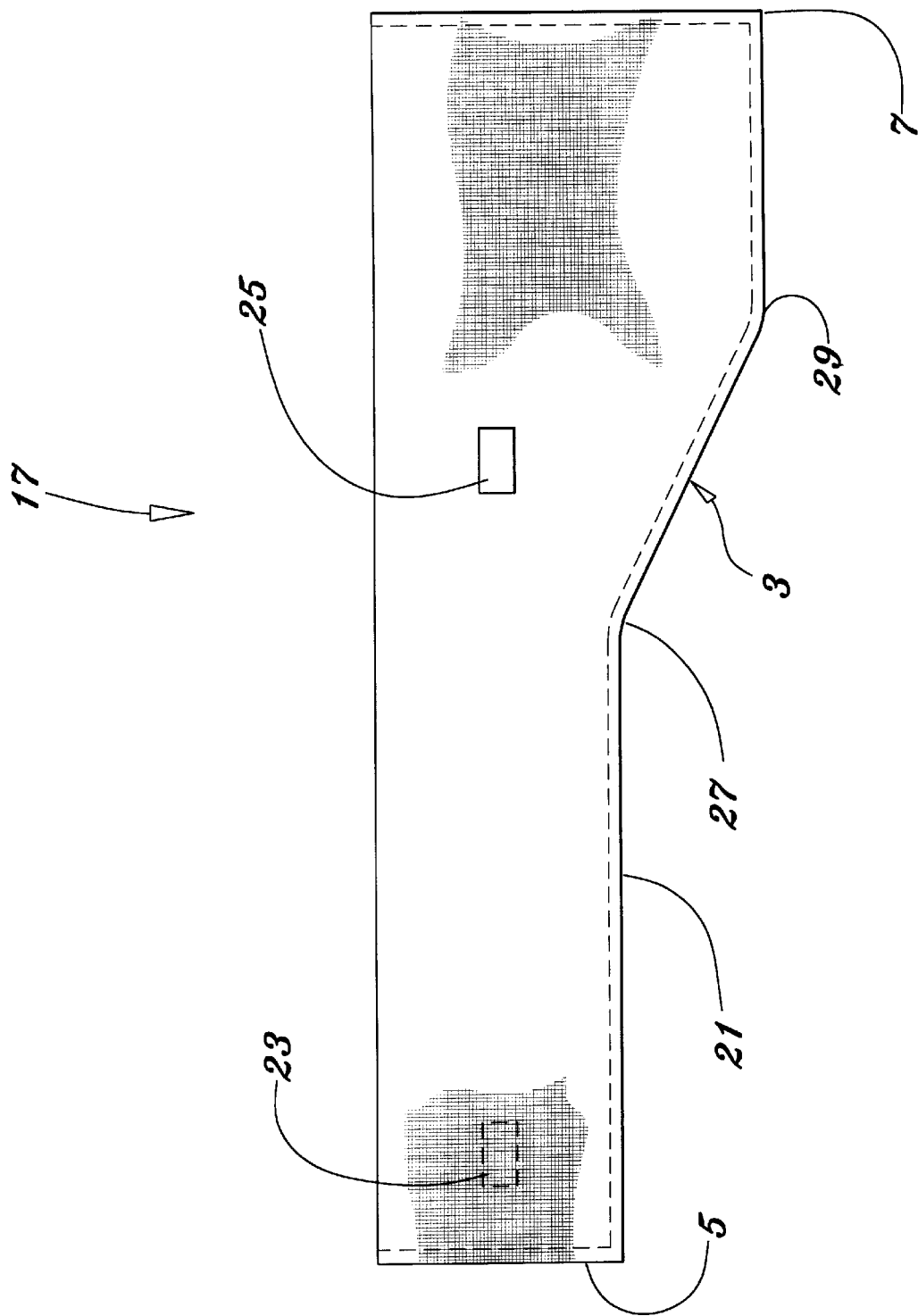

THERAPEUTIC WRAP FOR SORE THROATS

BACKGROUND OF THE INVENTION

1. Field of the Invention

The present invention relates generally to therapeutic wraps, and specifically to a therapeutic wrap adapted to use with a vaporizing ointment for treating colds and sore throats. The invention also includes a therapeutic kit and a method of treating colds and sore throats.

2. Description of the Related Art

Ailments of the upper respiratory tract, such as the common cold, frequently involve sore throats. Various types of vaporizing ointments are widely used in relieving the discomfort accompanying colds and sore throats. An example is Vicks VapoRub. Vaporizing ointments are generally applied to the throat and chest of the patient. These ointments typically include ingredients which open the pores and make the throat and chest feel warm. The warmth helps the patient to feel more comfortable.

Vaporizing ointments also include various vaporizing ingredients. The vaporizing ingredients may have a decongestant effect so that the patient feels he is breathing easier. The vaporizing ingredients may also include perfumes of various sorts, which help to distract and relax the patient. Typical ingredients of a vaporizing ointment include menthol, camphor, eucalyptus oil, and spirits of turpentine.

The instructions for using a vaporizing ointment typically state that the ointment should be rubbed on throat and chest as desired. The instructions suggest that the ointment may then be covered with a dry, warm cloth. Covering the ointment also prevents the ointment from staining the patient's clothing.

While any available cloth may be used for covering in this way, such as a towel, diaper, or scarf, such improvised wraps have a number of disadvantages. Improvised wraps tend to be bulky and unattractive. They fit poorly under a patient's normal clothing. These problems generally limit the use of vaporizing ointments to the home or similarly private situations where loose-fitting clothing is appropriate.

Since improvised wraps are not designed to wrap around the neck, they may not wrap closely, creating gaps and drafts. The cold air reaching the open pores of the patient's skin is unpleasant and tends to counteract the beneficial feeling of warmth from the ointment. Since improvised wraps are not secured around the neck, they may even fall off, particularly if the patient moves around. This tends to limit the patient's mobility. If the vaporizing ointment has been applied to both the throat and the chest, it can be difficult to arrange an improvised wrap so that both the throat and chest are securely covered. Some of the beneficial feeling of warmth is lost. The ointment may also stain the patient's clothing where the ointment has not been fully covered.

U.S. Pat. No. Des. 342,790 shows a therapeutic neck wrap having fasteners for fastening around the neck. U.S. Pat. No. 4,805,619 discloses a therapeutic scarf for applying ice to the neck and chest during hot weather and vigorous activity. U.S. Pat. No. 5,005,374 discloses a thermal wrap for containing hot or cold pack inserts. U.S. Pat. No. 5,088,549 discloses a neckband which is tied around the neck for heating or cooling the user. U.S. Pat. No. 5,507,793 discloses a neck wrap for cooling or heating the neck which drapes down the chest and is secured with hook and loop fastener.

None of the above inventions and patents, taken either singularly or in combination, is seen to describe the instant invention as claimed. Thus a therapeutic wrap for colds and sore throats solving the aforementioned problems is desired.

SUMMARY OF THE INVENTION

The present invention is a therapeutic wrap adapted to use with a vaporizing ointment for treating colds and sore throats. The invention includes a therapeutic kit having a vaporizing ointment and a wrap, and a method of treating colds and sore throats. The wrap is composed of an elongated piece of fabric, preferably flannel. Flannel feels warm and comfortable, is easily washed, yet looks neat.

The fabric has a throat end and a chest end. The throat end has a width approximately corresponding to the length of a human neck. The chest end has a width greater than the width of the throat end. At least two mating portions of hook and loop fastener are attached to opposite surfaces of the fabric. The hook and loop fastener secures the wrap around the neck so that the chest end drapes over the chest. The wrap is comfortable, looks neat, and holds securely, so that the patient's mobility is enhanced.

Accordingly, it is a principal object of the invention to provide a therapeutic wrap adapted to use with a vaporizing ointment for relieving the discomfort of a cold or sore throat by making the throat and chest of a patient feel warm, making the patient feel his breathing is eased, and/or relaxing and distracting the patient.

It is a further object of the invention to provide a therapeutic wrap for use with a vaporizing ointment which prevents drafts from reaching the neck and chest, allows the patient to move about freely, and is appropriate for social wear.

It is a further object of the invention to provide a therapeutic wrap which secures closely to the patient's neck and chest, fits neatly without bulk under a patient's normal clothing, is easily washed, and prevents a vaporizing ointment applied to the neck and chest from penetrating or staining the clothing.

Still another object of the invention is to provide a convenient therapeutic kit for treating colds and sore throats, including a vaporizing ointment and a wrap.

Another object of the invention is to provide a method for treating colds and sore throats by applying a vaporizing ointment to the neck and chest, covering the neck and chest with a wrap, and securing the wrap with hook and loop fastener.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 3 is a view of the second surface of a therapeutic wrap.

Similar reference characters denote corresponding features consistently throughout the attached drawings.

DETAILED DESCRIPTION OF THE PREFERRED EMBODIMENTS

The present invention is a therapeutic wrap adapted to use with a vaporizing ointment for treating colds and sore throats. The invention includes a therapeutic kit having a vaporizing ointment and a wrap, and a method for treating colds and sore throats.

Figure 1:
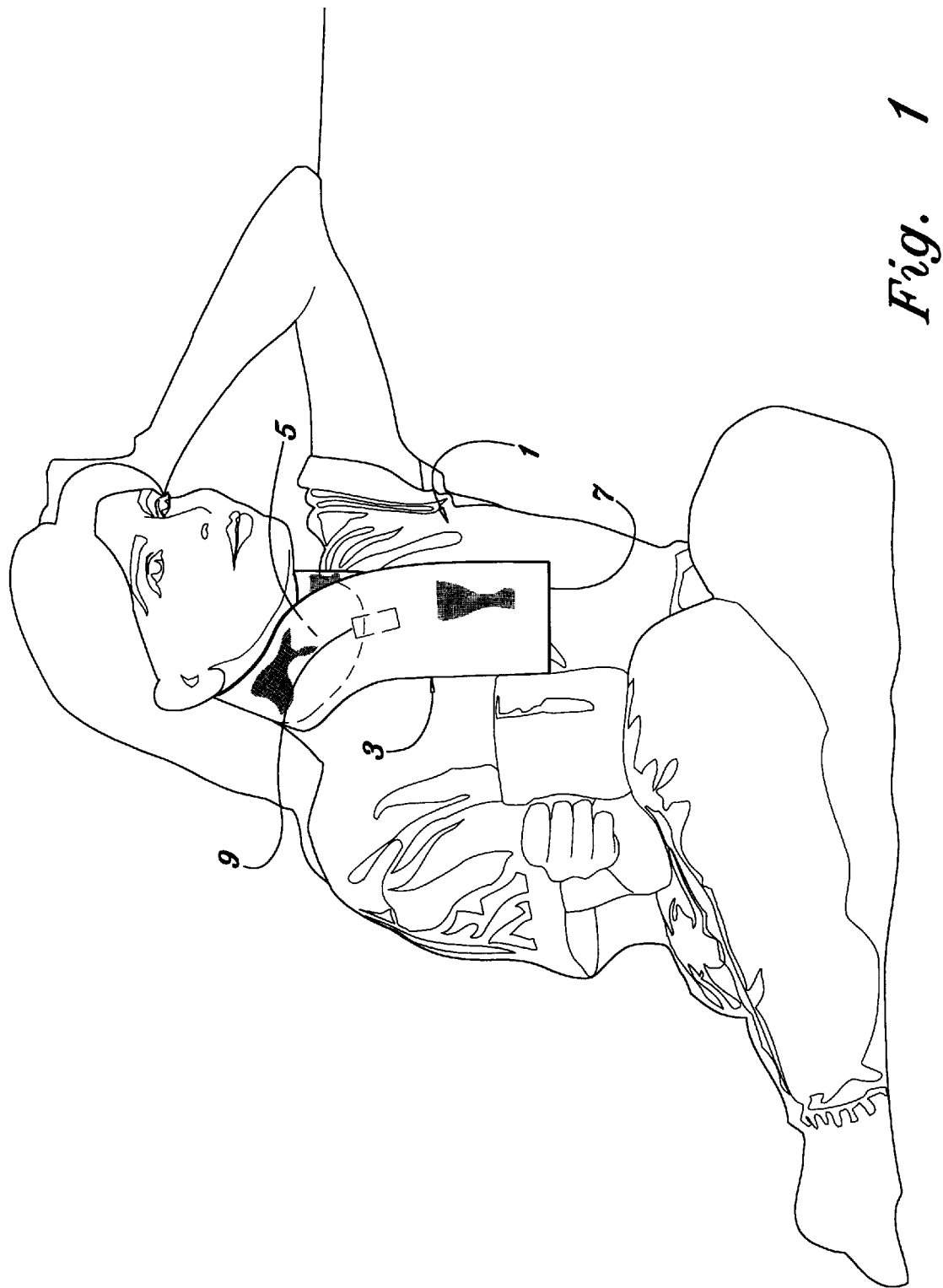
FIG. 1 is an environmental, perspective view of a therapeutic wrap for colds and sore throats according to the present invention.

FIG. 1 is an environmental, perspective view of a therapeutic wrap 1 according to the present invention. The wrap 1 is adapted to use with a vaporizing ointment for treating colds and sore throats. The wrap 1 includes an elongated piece of fabric 3 adapted to wrapping the neck and chest of a patient. The patient's neck has a length and a circumference. The patient's chest has a length extending roughly from the collarbone to the bottom of the rib cage (not shown).

The fabric 3 has a throat end 5 and a chest end 7. The fabric 3 has a length from the throat end 5 to the chest end 7. The throat end 5 is located at the front of the patient's neck. The wrap 1 wraps counterclockwise around the patient's neck and drapes over the chest. The fabric 3 has a first planar surface, and a second planar surface opposite the first surface. For the wrap 1, the first surface is an outer surface. The second surface of wrap 1 is an inner surface, in contact with the neck and chest. The throat end is covered by the remainder of the wrap 1. This helps the wrap to fit neatly under the patient's clothing.

The throat end 5 has a width corresponding to the approximate neck length. The chest end 7 has a width greater than the width of the throat end 5. The wrap 1 is secured around the neck by hook and loop fastener 9 so that the chest end 7 drapes over the chest.

The use of the wrap 1 with the vaporizing ointment 13 has many advantages over ointment alone or ointment used with an improvised wrap such as a towel or a diaper. The wrap 1 covers the neck and chest effectively without bulk and without gaps. The neck and chest are protected from drafts. The wrap 1 cannot fall off, no matter how much the patient moves around. This enhances the patient's mobility. The wrap 1 enhances the effect of the vaporizing ointment 13 in relieving colds and sore throats by making the throat and chest feel warm. The wrap 1 does not interfere with the decongestant effect of the vapors from the vaporizing ointment 13. The patient feels his breathing is eased. The feeling of warmth provided by the closely secured wrap helps to relax and distract the patient so that he feels more comfortable. Relaxation also helps the patient to breathe more easily.

The wrap 1 fits neatly under the patient's normal clothing. Loose-fitting clothing is not necessary. The appearance of the wrap 1 under clothing is similar enough to a turtleneck or similar garment that the wrap is appropriate for social wear. The patient is not restricted to his home or similarly private situations. The patient's normal clothing is protected from the vaporizing ointment. The wrap 1 itself can be easily washed.

Figure 2:
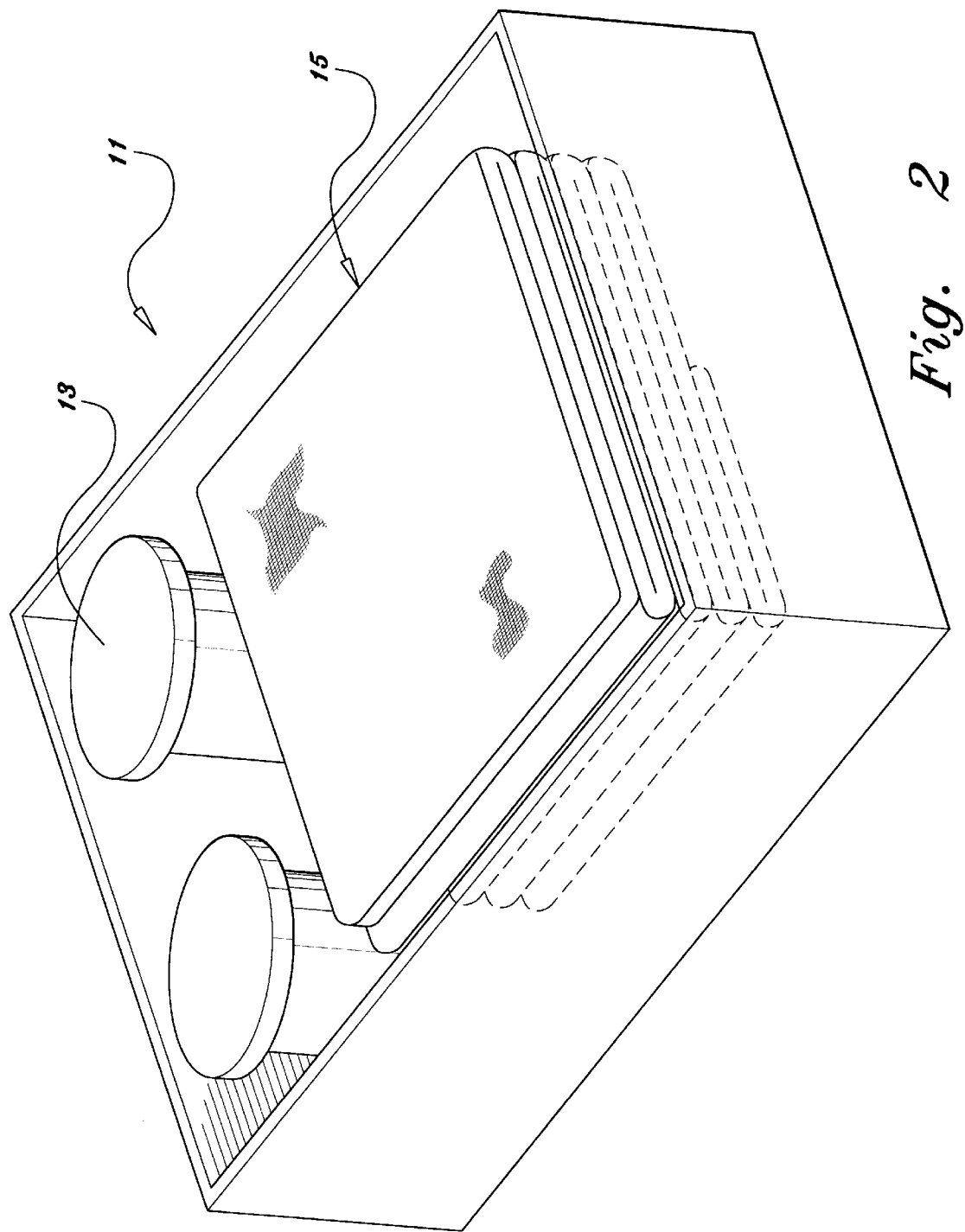
FIG. 2 is a perspective view of a therapeutic kit for treating colds and sore throats.

FIG. 2 is a perspective view of a therapeutic kit 11 for treating colds and sore throats. The therapeutic kit 11 comprises in combination a vaporizing ointment 13 and a second embodiment 15 of the wrap. The wrap 15 is adapted to wrapping the neck and chest of a patient. The wrap 15 includes an elongated piece of fabric. Since the jars of vaporizing ointment 13 and the wrap 15 are packaged as a kit, both are conveniently available for use together. After use, the vaporizing ointment 13 and the wrap 15 may be stored together. Both are therefore easy to locate when a patient has a sore throat.

FIG. 3 is a view of the second surface of a third embodiment 17 of a therapeutic wrap. The elongated piece of fabric 3 extends from the throat end S to the chest end 7. Preferably the fabric 3 is flannel. The fabric 3 has a chin edge 19 and a shoulder edge 21. The fabric 3 has a width from the chin edge 19 to the shoulder edge 21. Preferably the fabric 3 has a fold at the chin edge 19 so that the fabric 3 has two fabric layers.

The therapeutic wrap 17 has at least two mating portions of hook and loop fastener 9. The first mating portion 23 is attached to the fabric 3 near the throat end 5 on the first surface, and so is shown in phantom. The distance from the throat end 5 to the first mating portion 23 is preferably about one inch. The corresponding second mating portion 25 is attached to the fabric on the second surface. For wrap 17, the first surface is an outer surface and the second surface is an inner surface, in contact with the neck and chest of the patient. The wrap 17 wraps clockwise from the throat end around the patient's neck. The distance between the first and second mating portions 23 and 25 corresponds to the approximate circumference of the neck of the patient.

The first mating portion 23 preferably has a length of at least two inches. The second mating portion 25 preferably has a length of at least one inch. This arrangement allows for adjustment so that a single wrap can fit patients having somewhat different neck sizes.

The first mating portion 23 preferably is attached to the fabric 3 at a location somewhat closer to the chin edge 19 than to the shoulder edge 21. The second mating portion 25 is preferably located at a distance from the chin edge 19 approximately equal to that of the first mating portion 23. These locations help the wrap to fit neatly and closely to the patient's neck.

The second mating portion 25 is attached to the fabric 3 at a distance from the chest end 7 corresponding to the approximate length of the patient's chest. Preferably the first and second mating portions 23 and 25 of hook and loop fastener are attached to the fabric by stitching.

Preferably the width of the fabric 3 increases gradually from the throat end 5 to the chest end 7. The change in width has a beginning point 27 and an ending point 29 on the shoulder edge 21 of the fabric 3. Preferably the beginning point 27 has a distance from the throat end 5 of approximately $1/3$ to $1/2$ of the total fabric length. The ending point 29 preferably has a distance from the throat end 5 of approximately $1/2$ to $2/3$ of the total fabric length. The ending point 29 is preferably near the location of the second mating portion 25.

Preferably the wrap is provided in a variety of sizes. For all sizes, the width of the chest end 7 is preferably about 7½ inches. One preferred embodiment has a total fabric length of about 27 inches. The width of the throat end 5 is about 5½ inches. The change in width ends at a distance of about 10½ inches from the chest end 7. For another preferred embodiment, the fabric length is about 30 inches, the width of the throat end 5 is about 5½ inches, and the change in width ends at a distance of about 11½ inches from the chest end 7. For another preferred embodiment, the fabric length is about 36 inches, the width of the throat end 5 is about 6 inches, and the change in width ends at a distance of about 14½ inches from the chest end 7.

The invention includes a method for treating colds and sore throats. The method comprises three steps. The first step is applying a vaporizing ointment 13 to the neck and chest of a patient. The second step is covering the neck and chest with a wrap 17. The wrap 17 is composed of an elongated piece of fabric 3. The wrap 17 has a throat end 5 and a chest end 7. The throat end 5 has a width corresponding to the approximate neck length of the patient. The chest end 7 has a width greater than the width of the throat end 5.

The third step is securing the wrap 17 around the neck by mating at least two mating portions 23 and 25 of hook and loop fastener 9. The mating portions 23 and 25 are attached to opposite surfaces of the fabric. The mating portions 23 and 25 mate at the front area of the neck.

It is to be understood that the present invention is not limited to the embodiments described above, but encompasses any and all embodiments within the scope of the following claims.

We claim:

1. A therapeutic wrap adapted to use with a vaporizing ointment for treating colds and sore throats, comprising:
   (a) an elongated piece of fabric adapted to wrapping a neck and chest of a patient, the neck having a length and a circumference, the chest having a length, the fabric having two fabric layers, each fabric layer being composed of flannel, the fabric having a throat end, a chest end, a length from the throat end to the chest end, a chin edge, a shoulder edge, an outer surface, and an inner surface opposite the outer surface, the inner surface being adapted to contact the neck and chest, the throat end having a width corresponding to the approximate neck length, the chest end having a width greater than the width of the throat end, the chin edge being perpendicular to the throat end and to the chest end, the shoulder edge having a throat end portion, a chest end portion, and an intermediate portion, the throat and chest end portions of the shoulder edge being parallel to the chin edge, the intermediate portion of the shoulder edge being at an angle to the chin edge; and
   (b) at least two mating portions of hook and loop fastener, a first mating portion being attached to the fabric near the throat end on the outer surface, and the corresponding second mating portion being attached to the fabric on the inner surface, the distance between the first and second mating portions corresponding to the approximate neck circumference, the second mating portion being attached to the fabric at a distance from the chest end corresponding to the approximate chest length.

2. The therapeutic wrap according to claim 1, wherein:
   (a) the length of the throat end portion of the shoulder edge is approximately ⅓ to ½ of the fabric length, the length of the chest end portion of the shoulder edge is approximately ⅓ to ½ of the fabric length;
   (b) the width of the chest end is about 7½ inches; and
   (c) the first and second mating portions of hook and loop fastener are attached to the fabric by stitching.

3. The therapeutic wrap according to claim 2, wherein the fabric length is about 27 inches, the width of the throat end is about 5½ inches, and the change in width ends at a distance of about 10½ inches from the chest end.

4. The therapeutic wrap according to claim 2, wherein the fabric length is about 30 inches, the width of the throat end is about 5½ inches, and the change in width ends at a distance of about 11½ inches from the chest end.

5. The therapeutic wrap according to claim 2, wherein the fabric length is about 36 inches, the width of the throat end is about 6 inches, and the change in width ends at a distance of about 14½ inches from the chest end.

6. A therapeutic kit for treating colds and sore throats, comprising in combination:
   (a) a vaporizing ointment; and
   (b) a wrap, the wrap being adapted to wrapping a neck and chest of a patient, the neck having a length and a circumference, the chest having a length, the wrap having
      (i) an elongated piece of fabric, the fabric having two fabric layers, each fabric layer being composed of flannel, the fabric having a throat end, a chest end, a length from the throat end to the chest end, a chin edge, a shoulder edge, an outer surface, and an inner surface opposite the outer surface, the inner surface being adapted to contact the neck and chest, the throat end having a width corresponding to the approximate neck length, the chest end having a width greater than the width of the throat end, the chin edge being perpendicular to the throat end and to the chest end, the shoulder edge having a throat end portion, a chest end portion, and an intermediate portion, the throat and chest end portions of the shoulder edge being parallel to the chin edge, the intermediate portion of the shoulder edge being at an angle to the chin edge; and
      (ii) at least two mating portions of hook and loop fastener, a first mating portion being attached to the fabric near the throat end on the outer surface, and the corresponding second mating portion being attached to the fabric on the inner surface, the distance between the first and second mating portions corresponding to the approximate neck circumference, the second mating portion being attached to the fabric at a distance from the chest end corresponding to the approximate chest length.

7. A method for treating colds and sore throats, comprising the steps of:
   (a) applying a vaporizing ointment to a neck and chest of a patient;
   (b) covering the neck and chest with a wrap, the wrap being composed of an elongated piece of fabric, the fabric having two fabric layers, each fabric layer being composed of flannel, the wrap having a throat end, a chest end, a chin edge, a shoulder edge, an outer surface, and an inner surface opposite the outer surface, the inner surface being adapted to contact the neck and chest, the throat end having a width corresponding to the approximate neck length, the chest end having a width greater than the width of the throat end, the chin edge being perpendicular to the throat end and to the chest end, the shoulder edge having a throat end portion, a chest end portion, and an intermediate portion, the throat and chest end portions of the shoulder edge being parallel to the chin edge, the intermediate portion of the shoulder edge being at an angle to the chin edge; and
   (c) securing the wrap around the neck by mating at least two mating portions of hook and loop fastener, a first mating portion being attached to the fabric near the throat end on the outer surface, and the corresponding second mating portion being attached to the fabric on the inner surface, the mating portions mating at the front area of the neck.

* * * * *